US00PP36719P2

(12) United States Plant Patent
Kolster et al.

(10) Patent No.: US PP36,719 P2
(45) Date of Patent: Jun. 3, 2025

(54) ***HYDRANGEA* PLANT NAMED 'Hokomamipe'**

(50) Latin Name: *Hydrangea macrophylla*
Varietal Denomination: Hokomamipe

(71) Applicants: Kolster Holding B.V., Boskoop (NL); Horteve Breeding B.V., Aalsmeer (NL)

(72) Inventors: Peter Rudolf Kolster, Boskoop (NL); Cornelis Pieter Eveleens, Aalsmeer (NL)

(73) Assignees: KOLSTER HOLDING BV, Boskoop (NL), part interest; HORTEVE BREEDING BV, Aalsmeer (NL), part interest ( * ) Notice: Subject to any disclaimer, the term of this patent is extended or adjusted under 35 U.S.C. 154(b) by 0 days.

(21) Appl. No.: 18/805,682

(22) Filed: Aug. 15, 2024

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

(56) References Cited

U.S. PATENT DOCUMENTS

PP34,143 P2 * 4/2022 Eveleens ..... A01H 6/48
Plt./250

OTHER PUBLICATIONS https://online.plantvarieties.eu/publicConsultationDetails?registerId=20231584&denomination=hokomamipe.*

* cited by examiner

*Primary Examiner* — Susan McCormick Ewoldt
(74) *Attorney, Agent, or Firm* — Penny J. Aguirre

(57) ABSTRACT

A new cultivar of *Hydrangea macrophylla* plant named 'Hokomamipe' that is characterized by its very dark green-black foliage, its inflorescences with sterile flower sepals that are clear white in color with light pink margins when mature. its sterile flower sepals with moderately serrated margins, and its compact plant habit.

2 Drawing Sheets

Botanical classification: *Hydrangea macrophylla.*
Varietal denomination: 'Hokomamipe'.

CROSS REFERENCE TO A RELATED APPLICATION

This application is related to a European plant breeders' rights application filed on Jul. 27, 2023, application No. 2023/1584. The Applicant received the information for the Plant breeders' rights application directly from the Inventor.

BACKGROUND OF THE INVENTION

The present invention relates to a new and distinct cultivar of *Hydrangea macrophylla* and will be referred to hereafter by its cultivar name, 'Hokomamipe'. 'Hokomamipe' represents a new bigleaf *Hydrangea*, a perennial shrub grown for use in the landscape and as a potted plant.

'Hokomamipe' derived from an ongoing controlled breeding program directed by the Inventors. A goal of the breeding program was to develop a new cultivar of *Hydrangea* with dark leaves and light pink to white inflorescences.

'Hokomamipe' arose from a controlled cross made by the Inventors in Boskoop, The Netherlands in June of 2015 between unnamed and unpatented proprietary plants from the Inventors' breeding program; the female parent designated as accession No. 12-066-051 and the male parent designated as accession No. 13-012-001. 'Hokomamipe' was selected as a single unique plant from amongst the resulting seedlings in May of 2017.

Asexual propagation of the new cultivar was first accomplished by stem cuttings by one of the Inventors in August of 2017 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokomamipe' as a unique cultivar of *Hydrangea macrophylla.*

1. 'Hokomamipe' exhibits very dark green-black foliage.
2. 'Hokomamipe' exhibits inflorescences with sterile flower sepals that are clear white in color with light pink margins when mature.
3. 'Hokomamipe' exhibits sterile flower sepals with moderately serrated margins.
4. 'Hokomamipe' exhibits a compact plant habit.

The female parent of 'Hokomamipe' differs from 'Hokomamipe' in having leaves that are lighter green in color and inflorescences with sterile flower sepals that are more bi-colored. The male parent of 'Hokomamipe' differs from 'Hokomamipe' in having inflorescences with sterile flower sepals light pink in color and leaves that are sturdier and lighter green in color. 'Hokomamipe' can be most closely compared to the *Hydrangea macrophylla* cultivars 'Hokomaginfe' (Not patented) and 'Hokomabebos' (U.S. Pat. No. 34,143). 'Hokomaginfe' is similar to 'Hokomamipe' in having inflorescences with sterile sepals that are bi-colored and dark green foliage. 'Hokomaginfe' differs from 'Hokomamipe' in having inflorescences with sterile flower sepals that are picotee in coloration with smooth margins. 'Hokomabebos' is similar to 'Hokomamipe' in having inflorescences with sterile sepals that are bi-colored. 'Hokomabebos' differs from 'Hokomamipe' in having inflorescences with sterile sepals with deep pink-red margins and deep green foliage with a burgundy blush.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plants Nouveau, Plantarium/Groen-Direkt, Hortweek, Plantago, Kolster B.V. (linkedin), Arboretum Wojslawice, Floraccess, Holland House Nursery, and D and M Garden Centre.

BRIEF DESCRIPTION OF THE DRAWINGS

The accompanying color photographs illustrate the overall appearance and distinct characteristics of the new *Hydrangea*. The photographs were taken of a two-year-old plant of 'Hokomamipe' as grown outdoors in 20-cm containers in Vineland Station, Ontario, Canada.

The photograph in FIG. 1 provides a side view of 'Hokomamipe' in bloom with mature inflorescences.

Figure 1:
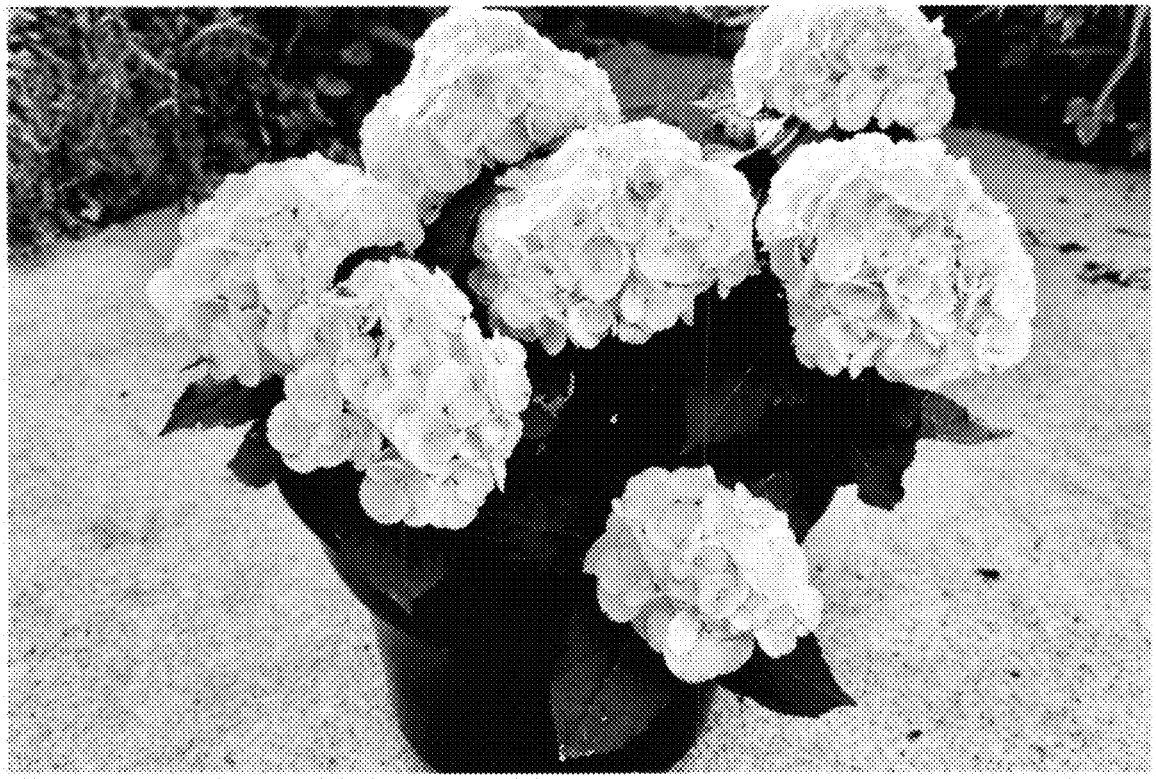
Figure 2:
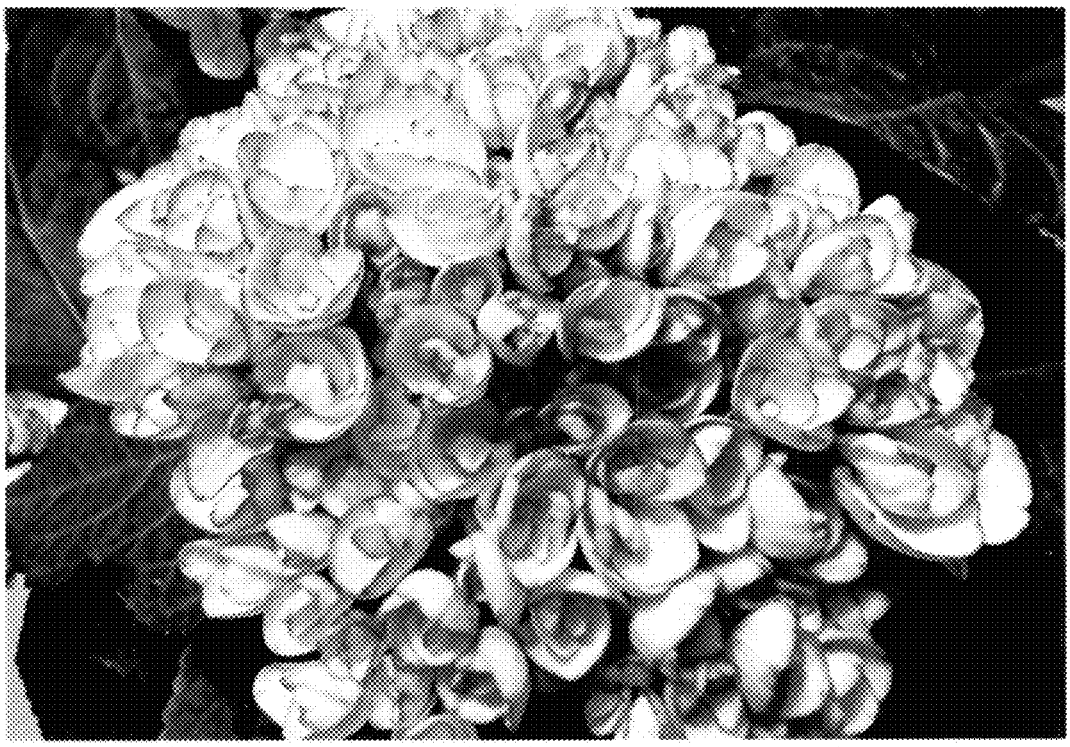

The photograph in FIG. 2 provides a provides a close-up view of an immature inflorescence of 'Hokomamipe'.

Figure 3:
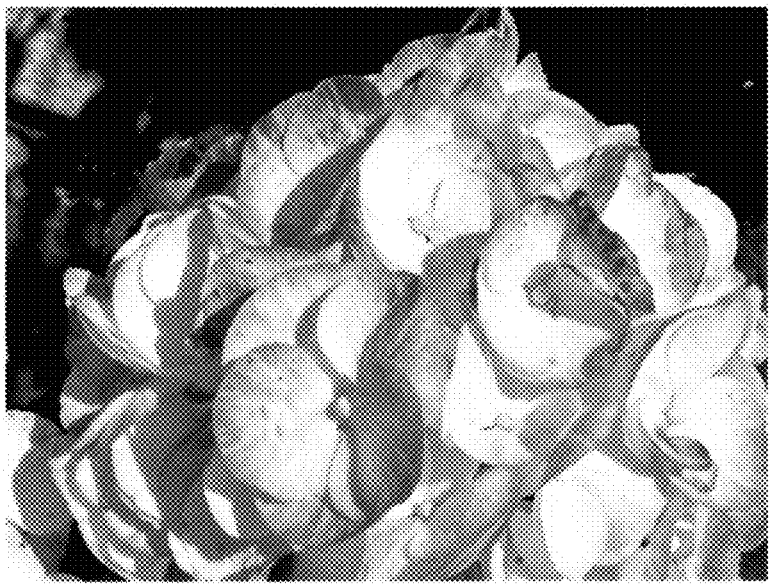

The photograph in FIG. 3 provides a close-up view of an aging inflorescence of 'Hokomamipe'.

Figure 4:
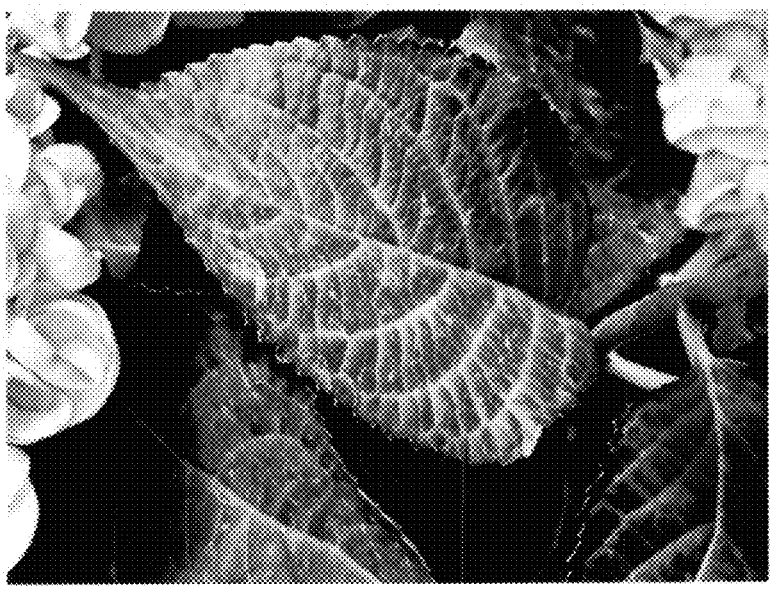

The photograph in FIG. 4 provides a close-up view of the foliage of 'Hokomamipe'.

The colors in the photographs are as close as possible with the photographic and printing technology utilized and the color values cited in the detailed botanical description accurately describe the colors of the new *Hydrangea.*

BOTANICAL DESCRIPTION OF THE PLANT

The following is a detailed description of two-year-old plants of 'Hokomamipe' as grown outdoors in 20-cm containers in Vineland Station, Ontario, Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Late spring to late summer with flowers showy at least for 2 months in The Netherlands.

*Plant type.*—Deciduous shrub, mophead type *Hydrangea.*

*Plant habit.*—Upright.

*Height and spread.*—An average of 32 cm in height and 50 cm in spread as a one-year-old plant grown in a container and reaches 1 m in height and spread as a 3-year-old plant in the landscape.

*Hardiness.*—At least in U.S.D.A. Zones 5 to 9.

*Diseases and pests.*—No susceptibility and resistance to diseases or pests has been observed.

*Root description.*—Fine and fibrous, 161C in color.

*Propagation.*—Stem cuttings.

*Root development.*—An average of 6 weeks for root initiation with a young rooted plant produced in an average of 18 weeks.

*Growth rate and vigor.*—Moderate.

Branch description:

*Branch shape.*—Rounded.

*Branch strength.*—Strong.

*Branch color.*—Young; 144B, mature; 146B, old bark; N200A and N199B.

*Branch size.*—An average of 17 cm in length (excluding inflorescence) and 7 mm in diameter.

*Branch surface.*—Young branches slightly glossy, glabrous, older stems matte, glabrous, branches are moderately to densely covered with lenticels; linear and thin in shape, average of 35 per 1 cm diameter, average of 2 mm in length, 0.3 mm in width, 200A in color.

*Branch aspect.*—Held upright to slightly outward.

*Internode length.*—An average of 4 cm.

*Branching.*—Freely branching with an average of 3 lateral branches.

Foliage description:

*Leaf shape.*—Ovate to broadly ovate.

*Leaf arrangement.*—Opposite.

*Leaf division.*—Simple.

*Leaf base.*—Short attenuate.

*Leaf apex.*—Short apiculate.

*Leaf margins.*—Coarsely serrate.

*Leaf venation.*—Pinnate, color; upper surface 144A, lower surface 145B, main vein 145C.

*Leaf size.*—Up to 9 cm in length and 5.5 cm in width.

*Leaf attachment.*—Petiolate.

*Leaf number.*—An average of 8 to 10 per lateral stem.

*Leaf surface.*—Upper surface; leathery appearance, rugose, matte with a faint sheen, glabrous, lower surface; matte, glabrous with a faint sheen.

*Leaf color.*—Young and mature foliage; upper surface 202A with under tones of 135A, lower surface 138B, lightly flushed with 147A around the outsides, edges of margins 202A.

*Petioles.*—An average of 1.5 cm in length and 2 mm in diameter, upper and lower surface color 144A, both surfaces are glabrous and glossy.

Inflorescence description:

*Inflorescence type.*—Terminal panicle, full mophead in form, comprised of fertile flowers and sterile flowers.

*Lastingness of inflorescence.*—Persistent, in color for 2 months.

*Inflorescence number.*—One per lateral.

*Inflorescence size.*—Average of 8 cm in height, 14 cm in diameter.

*Flower number.*—Average of 170 sterile flowers and 70 fertile flowers per panicle.

*Flower fragrance.*—Very faint fresh fragrance.

*Flower aspect.*—Upright to outward.

*Flower size*.—Sterile flowers; an average of 2 cm in diameter, 1 cm in depth, fertile flowers; do not open.

*Flower type*.—Rotate.

*Flower buds*.—Sterile flowers; average of 3 mm in width and 2 mm in depth, obovate in shape, color 145A, flushed at the center with 185A, fertile flowers; average of 2 mm in width and depth, round in shape, color when young; 145A, flushed at the center with 185A, color when mature before dropping; 145A.

*Peduncles*.—Moderately strong, flexible, average of 2 cm in length and 2 mm in width, color; 144A, sparsely covered with lenticels; linear and thin in shape, average of 5 per 1 cm diameter, average of 1 mm in length, 0.3 mm in width, 144A in color, surface is glossy and densely covered with very minute pubescence.

*Pedicels*.—Moderately strong, flexible, average of 6 mm in length and 1.5 mm in width, color; 145D, surface is glossy and densely covered with very minute pubescence.

*Petals*.—Sterile flowers; petal spot (flower bud); 1.5 mm in depth and 1 mm in diameter, round in shape, color; 150C to 150D, becoming flushed with 68A, when petals open; average of 4, concave in shape, acute apex, cuneate base, entire margins, average of 2 mm in length, 1.5 mm in width, both surfaces are glabrous and matte, color: both surfaces when opening and fully open NN155B, fall colors; petals drop after full maturity, fertile flowers; petals do not open

*Sepals*.—Sterile flowers; showy, 5, reniform in shape, strongly overlapping, rotate in arrangement, margins moderately undulate and serrated, apex is very slightly retuse, cuneate base, average of 1.1 cm in length, 1.3 cm in width, both surfaces are glabrous, matte, and satiny, color: when opening upper and lower surface; 142A, edges of margins 183A and 185A, when fully open upper and lower surface; 157A, margins 185A and 186C, as the sepals age turning to 155C with margins moderately to heavily flushed with 68A.

Reproductive organs:

*Gynoecium*.—Sterile flowers; 1 pistil, an average of 1.5 mm in length, cone shaped, stigma; very small, rounded, bifid, 0.5 mm in length, 155A in color, style; 0.8 mm in length, 157D in color, ovary is superior, 0.5 mm in depth, 158C in color, fertile flowers drop after budding, gynoecium and androecium not developed.

*Androecium*.—Sterile flowers; 8 to 9 stamens, filaments; an average of 3 mm in length and NN155D in color, anthers; club-shaped, an average of 0.8 mm in diameter, 0.5 in depth, N155C in color, pollen; low, 158C in color, fertile flowers drop after budding, gynoecium and androecium not developed.

*Fruit and seed*.—Not observed.

It is claimed:

1. A new and distinct cultivar of *Hydrangea* plant named 'Hokomamipe' substantially as herein illustrated and described.

* * * * *